United States Patent [19]

Kraeutle

[11] 4,161,114
[45] Jul. 17, 1979

[54] METHOD AND APPARATUS FOR MEASURING ADHESION OF PARTICULATE MATERIALS

[75] Inventor: Karl J. Kraeutle, China Lake, Calif.

[73] Assignee: The United States of America as represented by the Secretary of the Navy, Washington, D.C.

[21] Appl. No.: 897,237

[22] Filed: Apr. 17, 1978

[51] Int. Cl.$^2$ ............................................. G01N 25/00
[52] U.S. Cl. ........................................ 73/15.6; 73/845; 73/150 A
[58] Field of Search .................. 73/9, 15.4, 15.6, 64.4, 73/88 B, 95, 101, 150 A

[56] References Cited

U.S. PATENT DOCUMENTS

| | | | |
|---|---|---|---|
| 2,633,027 | 3/1953 | Bunnel | 73/432 |
| 2,720,106 | 10/1955 | Lippman, Jr. | 73/101 X |
| 3,043,131 | 7/1962 | Heneage | 73/64.4 |
| 3,538,758 | 11/1970 | Karper et al. | 73/101 |
| 3,580,065 | 5/1971 | Strittmtter et al. | 73/150 X |
| 3,693,420 | 9/1972 | Wray | 73/101 X |
| 3,798,962 | 3/1974 | Dibley et al. | 73/9 X |
| 3,820,384 | 6/1974 | Brill | 73/101 |
| 3,875,791 | 4/1975 | Fitzgerald | 73/59 |
| 3,939,701 | 2/1976 | Peschl | 73/101 |
| 3,965,722 | 6/1976 | Bagg et al. | 73/59 |
| 4,041,806 | 10/1976 | Klar | 73/15.6 |

FOREIGN PATENT DOCUMENTS 312189  10/1971  U.S.S.R. ..................................... 73/150

OTHER PUBLICATIONS

Kraeutle, "Method to Test Adhesion of Aluminum Particles during Subignition Heating ---", CPIA Publication 281, 12/76.

Primary Examiner—Herbert Goldstein
Attorney, Agent, or Firm—R. S. Sciascia; W. Thom Skeer; K. Pritchard

[57] ABSTRACT

Apparatus and a method are disclosed for measuring adhesion of particulate materials. A geometric object, such as a steel ball, is immersed in a sample of particulate material which is compacted to a predetermined density. The temperature of the sample is carefully controlled while the steel ball is pulled from the sample. The force required to pull the ball from the sample at a given temperature is recorded. Numerous tests conducted at different temperatures provide data to define a characteristic curve for a given particulate material The apparatus and method is particularly useful for measuring the adhesion of aluminum powder such as that used as fuel in rocket motor solid propellant.

13 Claims, 5 Drawing Figures

METHOD AND APPARATUS FOR MEASURING ADHESION OF PARTICULATE MATERIALS

BACKGROUND OF THE INVENTION

1. Field of the Invention

This invention pertains to apparatus and a method for measuring physical properties of particulate material. More particularly, the present invention pertains to apparatus and a method for measuring adhesion of particulate material.

2. Description of the Prior Art

In the art of rocket motor solid propellants, metallic powders are often included as fuel in various propellant formulations. One metallic powder which is often used is aluminum powder. Particles of commercially produced aluminum powders are covered with thin oxide layers. When such a powder is heated in the condition it is received from a commercial supplier, the particles tend to become sticky. The stickiness, or adhesion of particles to each other, influences the agglomeration and combustion behavior of the aluminum powder contained in a solid propellant. Accordingly, a method for controlling particle adhesion has been developed. The method comprises modifying and strengthening the aluminum oxide layers on the particles by means of heat treatment in an oxidative atmosphere.

Heretofore, there has not been a method of measuring particle adhesion in a way that is meaningful in solid rocket propellant research, although methods have been devised for measuring viscosity of molten plastics material, flow characteristics of granular materials, and viscosity of liquids. Commonly, viscosity measuring apparatus uses either a rotating probe immersed in the test liquid, or a calibrated aperture through which the test liquid drains.

SUMMARY OF THE INVENTION

The present invention overcomes the omissions in the prior art to supply a method and apparatus by which the adhesion of particulate materials, and in particular surface modified aluminum particles, may be measured as a function of temperature. Investigators may now judge suitability of a powder for propellant applications, or any other application where adhesion and sintering play important roles, such as in powder metallurgy. Surface modified aluminum particles are defined as aluminum particles having a coating of $Al_2O_3$ which has been thickened and strengthened by thermal treatment.

According to the present invention, a metal block is heated at a constant rate by a wire wound furnace. The block contains a sample tube which contains a sample of particulate material. A geometric object such as a steel ball, which is connected to a load cell by a piano wire, is embedded in the particulate material. The load cell is linked to a synchronous or synchron motor by a length of twine, cord or the like. The twine may be guided over pulleys for convenience. A thermocouple, a temperature programmer, a temperature controller, and a power supply maintain the metal block and contained sample at a preselected temperature after heating the block at a controlled rate.

After the sample reaches a predetermined temperature the synchronous motor is activated to wind the twine and apply tensile force to the steel ball. Output from the load cell is continuously recorded, as is the temperature of the particulate material. As the tensile force on the steel ball equals and exceeds the adhesive forces of the powder or particulate material under investigation, the steel ball pulls out of the powder sample. This pull is recorded as a function of time. This process is repeated at many different temperatures to produce data sufficient to enable the plot of a characteristic curve for a given particulate material.

Accordingly, it is an object of the present invention to provide a means for measuring the effect of temperature on the adhesiveness of one particle to another in a sample of particulate material.

It is also an object of the present invention to provide a means for monitoring the effectiveness of a particle adhesion control method comprising modifying and strengthening the aluminum oxide layers on aluminum particles by heat treatment in oxidative atmospheres.

BRIEF DESCRIPTION OF THE DRAWING

A complete understanding of the present invention and of the above and other objects thereof may be gained from a consideration of the following detailed description of the preferred embodiment thereof presented hereinbelow in connection with the accompanying drawing figures, in which.

DESCRIPTION OF THE PREFERRED EMBODIMENT

According to this invention, the adhesion of as-received and of surface modified aluminum particles, that is, aluminum particles having a coating of $Al_2O_3$ which has been thickened and strengthened by thermal treatment, is measured as a function of temperature to enable judgment of the suitability of those particles for use in propellant applications, or any other applications where adhesion and sintering play important roles. Such other applications may include powder metallurgy for example. Particle adhesion is measured by using apparatus for the type shown in FIG. 1.

Figure 1:
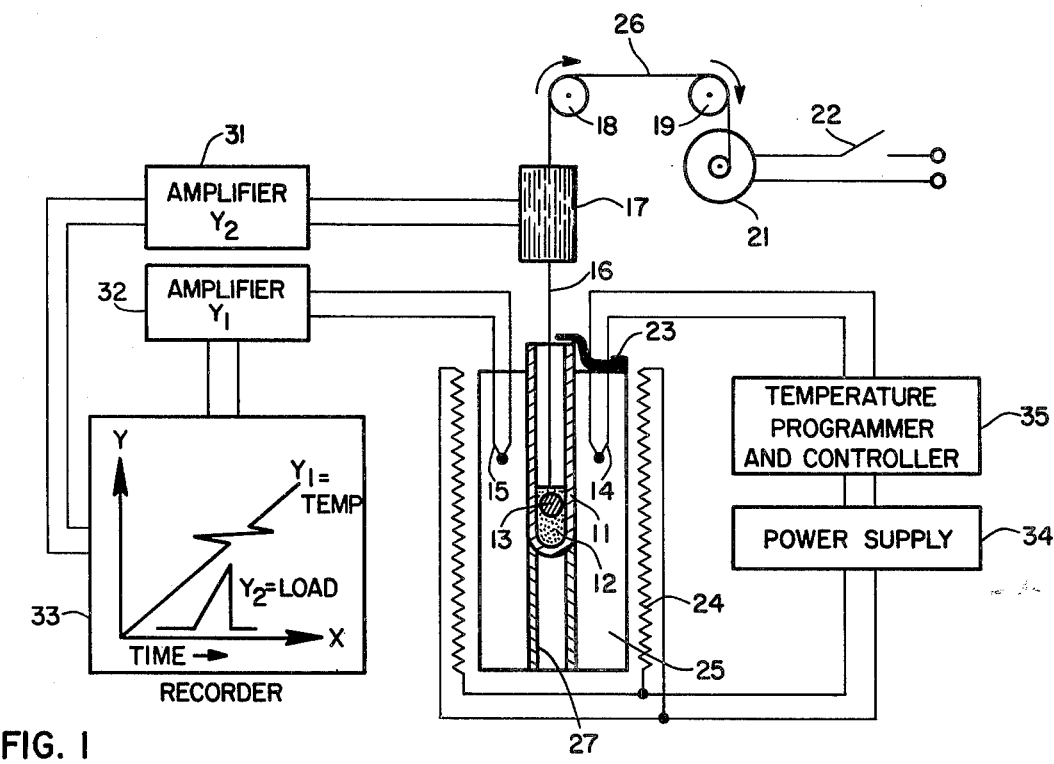
FIG. 1 illustrates apparatus suitable for practicing the method of this invention.

Referring now to FIG. 1 there is shown metallic block 25 which is retained within electric furnace 24. Electric furnace 24 receives electric energy from power supply 34 which is regulated by temperature programmer and controller 35. Thermocouple 14 senses temperature within block 25 and supplies this information to controller 35. Controller 35 regulates power supply 34 so as to maintain a preselected temperature in block 25. Inconel is one materal which may be used for metallic block 25. Thermocouple 15 also senses temperature within block 25 and transmits this information to amplifier 32 which drives one pen in chart recorder 33 so that a continuous record of block 25 temperature is recorded throughout the test. Temperature sensed by thermocouple 15 is recorded on a chart in recorder 33 along the curve labeled $Y_1$.

Sample container 11, which may be a pyrex tube, is mounted within block 25 at a predetermined point in a central well and is retained within the central well by bracket 23 which is attached to block 25. The central well in block 25 may be either a stepped hole or a constant diameter hole having spacer 27 inserted therein. Any equivalent means of supporting sample container 11 will work. Sample container 11 contains a quantity of particulate material 12 which is to be tested. Immersed within material 12 is a geometric object 13, which may be a steel ball or other geometric shape, a spherical shape being preferred. Piano wire 16 is attached to geometric object 13 on one end and is attached to load cell 17 on the other end. Line 26 is attached to load cell 17 and passes over pulleys 18 and 19 to synchronous motor 21. Synchronous motor 21 is configured to wind line 26 about a drum when motor 21 is activated. Line 26 may be string, wire, chain, twine, or the like. Switch 22 controls the flow of electric current to synchronous motor 21. Synchronous motor 21 is configured to wind line 26 about a drum when motor 21 is activated.

Load cell 17 produces a signal proportional to the tensile force exerted on it by piano wire 16. This signal is amplified by amplifier 31 and delivered to recorder 33 for recording on a chart along the curve labeled $Y_2$.

Figure 2:
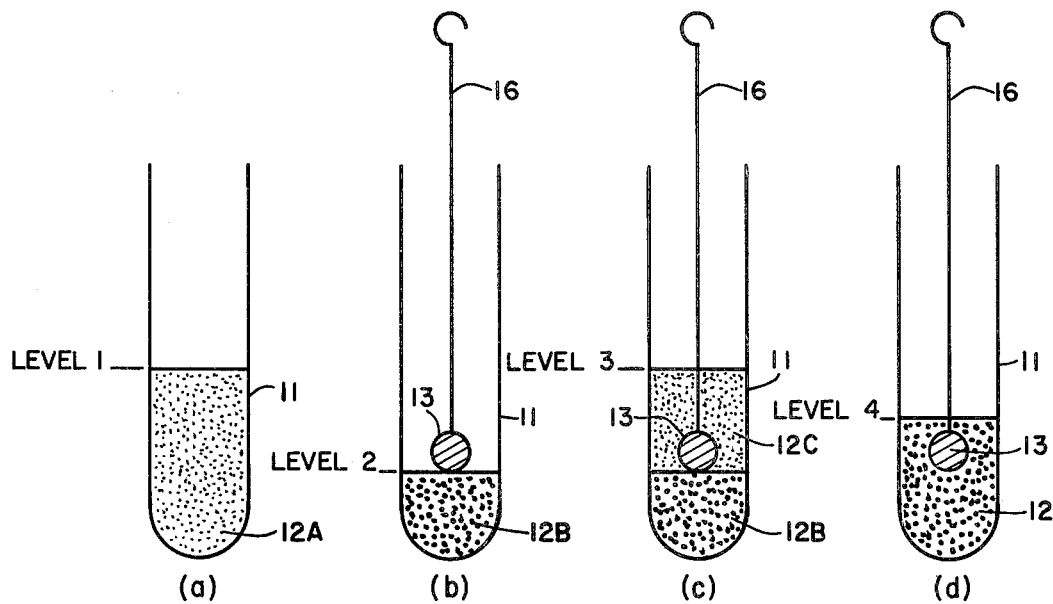
FIG. 2 illustrates the preparation of a sample of particulate material for measurement of adhesion in accordance with the present invention.

Referring now to FIG. 2 there is illustrated the preferred method of sample preparation to insure comparable and scientifically valid results. In FIG. 2A sample container 11 is shown partially filled with particulate material 12A to a first predetermined level. FIG. 2B shows particulate material 12B which is particulate material 12A after being packed to a predetermined density corresponding to its surface aligning with level 2. At this time geometric object 13 is rested and centered upon the surface of particulate material 12B. FIG. 2C illustrates additional particulate material 12C added to immerse geometric object 13. Particulate material 12C is added until its surface aligns with level 3. Finally, FIG. 2D shows particulate material 12 fully compacted to bring its surface to level 4, thereby providing a sample of particulate material having uniform density and an immersed geometric object. For convenience, a single sample container 11 such as a glass test tube may be permanently inscribed with lines identifying levels 1, 2, 3 and 4 for facilitating duplicate sample preparation. Any method of sample preparation may be used so long as the method used results in repeatable sample densities and immersed geometric objects. If the density of particulate material 12 is not uniform from one test to another, the results of a series of tests will lack scientific validity and will not be comparable or repeatable. No difficulties were encountered in keeping the powder sample in a pyrex tube under load which suggests that adhesion between glass and particles was similar to that between particles themselves. For temperatures in excess of 700° C., however, a metallic or ceramic sample container 11 may be required.

OPERATION

Referring again to FIG. 1 the method is practiced in the following manner. Sample container 11 is prepared with particulate material 12 and an embedded geometric object 13 as previously described. Sample container 11 is then inserted into a central well in block 25 and bracket 23 installed to retain container 11 in place. Piano wire 16 extending from geometric object 13 is attached to load cell 17. Temperature programmer and controller 35 regulates power from power supply 34 to wire wound furnace 24 to raise the temperature of particulate material 12 at a predetermined rate. A heating rate of approximately 40° centigrade per minute may be used. When the temperature within block 25 and particulate material 12 reaches a predetermined level as sensed by thermocouple 14, temperature programmer and controller 35 maintains that predetermined temperature. Thermocouple 15 simultaneously senses temperature in block 25 and by means of amplifier 32 and recorder 33 a permanent temperature time record $Y_1$ is made.

When the temperature in block 25 has stabilized, switch 22 is closed, activating synchronous motor 21. Motor 21, which may be a four revolution per minute synchronous motor, begins winding line 26 and thereby placing piano wire 16 under tension. As motor 21 continues to wind line 26 tensile force within piano wire 16 eventually equals and then exceeds the adhesive forces within particulate material 12 compacted over immersed geometric body 13. When this occurs, geometric body 13 is pulled from the particulate material 12. The tensile force within piano wire 16 is sensed by load cell 17 and recorded on recorder 33 by means of amplifier 31 in the form of plot $Y_2$.

Figure 3:
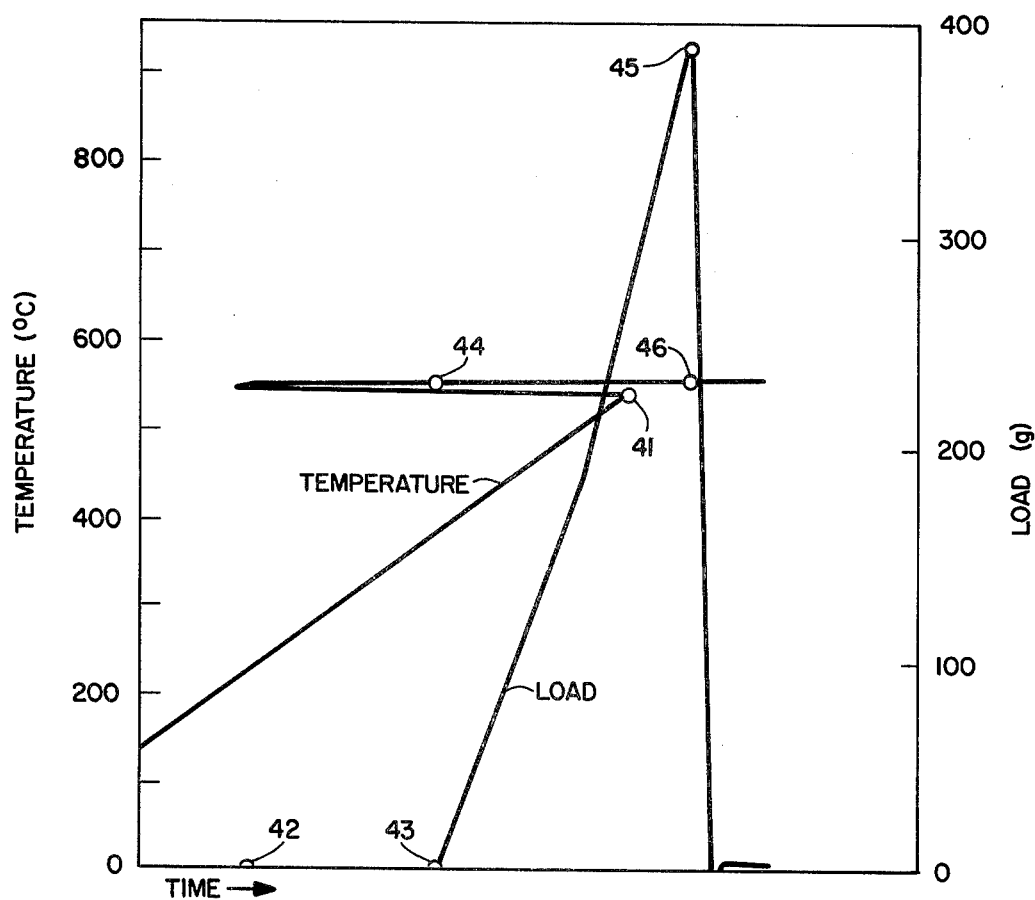
FIG. 3 illustrates a typical record of data derived from a single test according to the invention.

Referring now to FIG. 3 there is shown a typical plot of curves $Y_1$ and $Y_2$ for a single particulate material sample at a single temperature. As shown in FIG. 3 the temperature within block 25 and particulate material 12 gradually increases at a steady rate until point 41 is reached. At this point the time sweep rate of the chart recorder is increased to record with increased time resolution the temperature of the sample during tensile force application. As synchronous motor 21 is activated, as shown at point 42, slack in piano wire 16 is begun to be removed. At point 43 slack in piano wire 16 has been taken up and tensile stress begins to form within piano wire 16. Temperature at this time is shown at point 44. As the tensile force applied by piano wire 16 increases, as shown by the curve between points 43 and 45, temperature increases only slightly, as shown by the curve between points 44 and 46. At point 45 the tensile force applied by piano wire 16 begins to exceed the adhesive force present in the powder sample, and geometric object 13 begins to pull free. At this time, tensile force applied by piano wire 16 rapidly drops to a low level. The mean temperature between points 44 and 46 becomes the horizontal coordinate of a data point on a characteristic curve for this sample material, and the maximum load indicated at point 45 becomes the vertical coordinate of that same data point which is then plotted.

Figure 4:
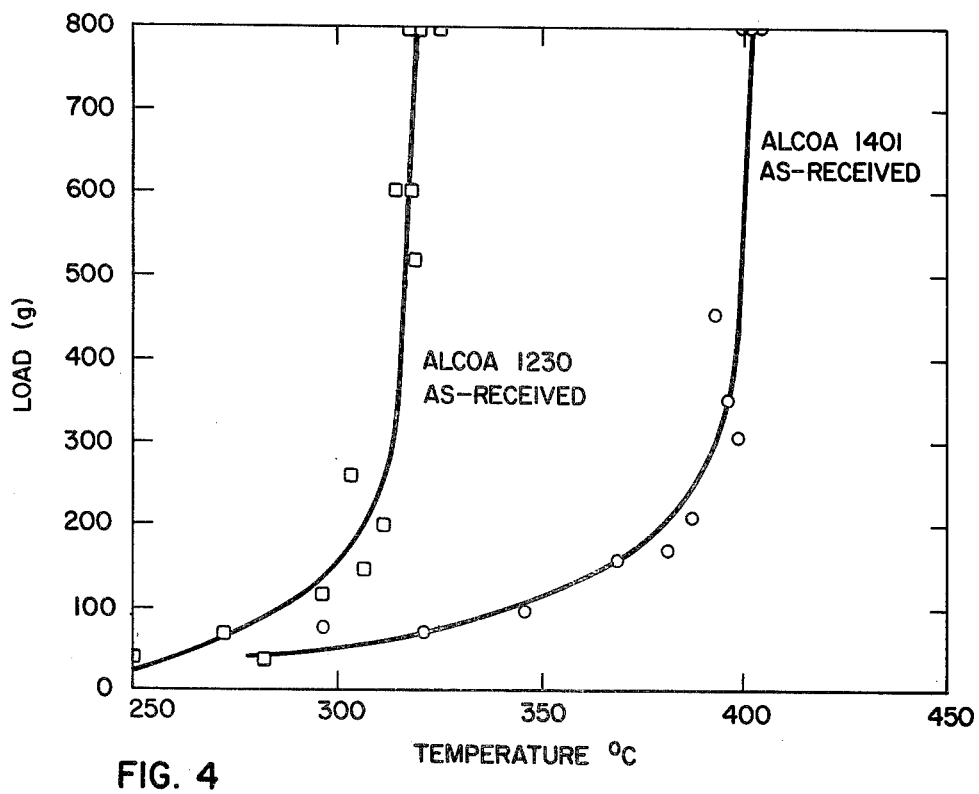
FIG. 4 illustrates a characteristic curve plotted for two different particulate materials as-received from a commercial supplier.
Figure 5:
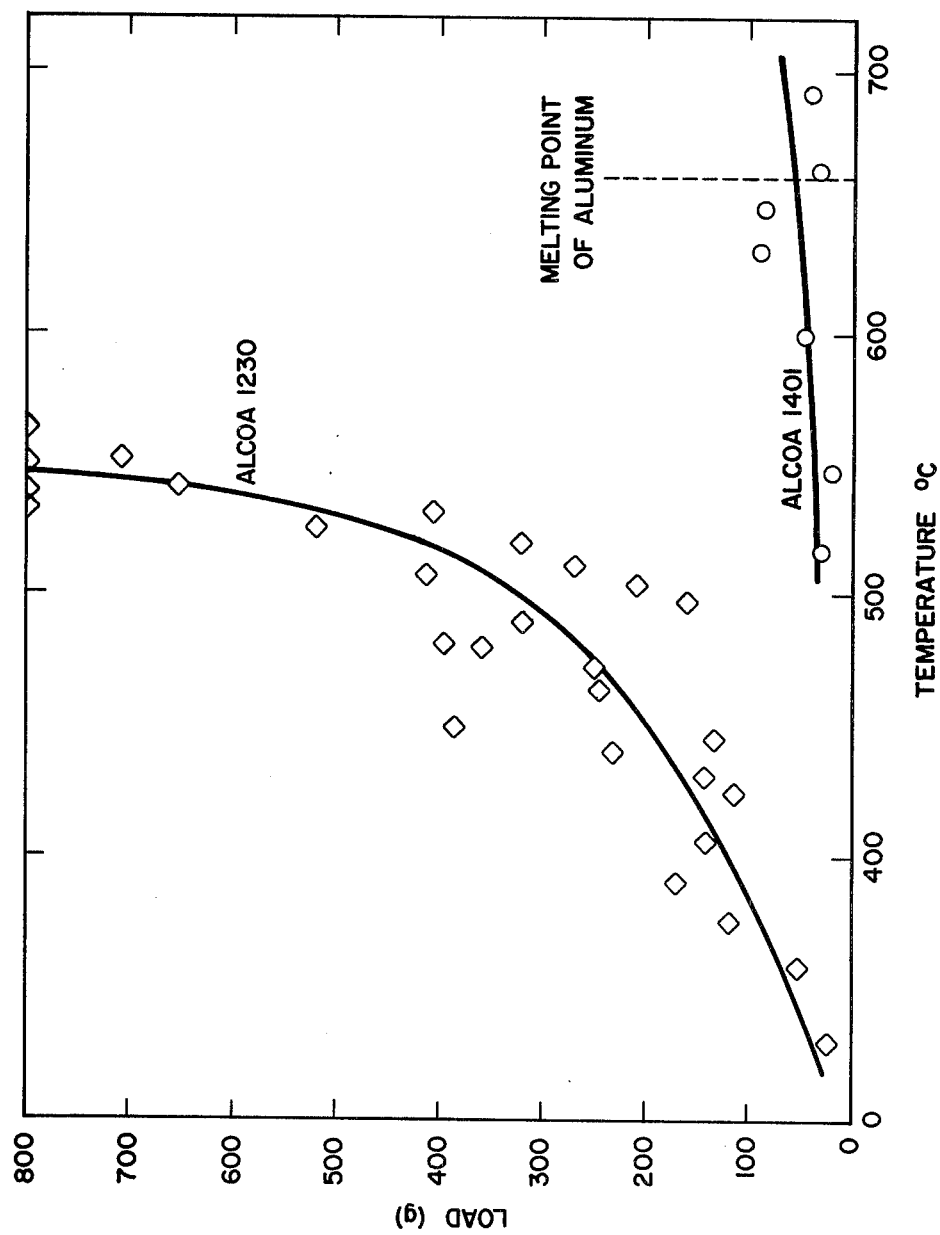
FIG. 5 illustrates characteristic curves for the particulate materials illustrated in FIG. 4 after undergoing preliminary surface oxide layer modification treatment.

This procedure is repeated many times for a given sample at different temperatures and each point plotted on a load versus temperature graph as shown in FIGS. 4 and 5.

Referring now to FIGS. 4 and 5 there is shown characteristic curves for two types of aluminum powder which were tested as-received and plotted in FIG. 4. After heat treatment of additional samples of these two powders according to the method by which oxide coatings upon individual particles are increased and strengthened, the samples were tested again and the results plotted in FIG. 5. Comparison of FIGS. 4 and 5 shows that the method of the present invention enables measurement of physical properties of the two powders which are related to their degree of adhesiveness, and it is readily seen that the heat treatment of the powders has effected a significant decrease in degree of adhesiveness at a given temperature.

In general, the heating rate applied to the sample can be varied with the temperature programmer if desired. Also, in preparing samples of particulate materials, the samples may be compacted within container 11 by tapping. The procedure for preparing samples previously described provides constant sphere or other geometric object location, and constant powder packing as required in a given test series.

The general shape of a curve in FIGS. 4 and 5 shows the adhesion behavior or particular powders as a function of temperature. For as received powder, a slow increase of adhesion, as characterised by load, is followed by a steep exponential-like increase in a narrow temperature range. Oxidation of aluminum power reduces the rate of increase of adhesion and moves the temperature of steep increase to higher values as shown in FIG. 5. It is known from combustion experiments with aluminized propellants that aluminum powders having strong adhesion at high temperatures, such as oxidized powders, show appreciably less agglomeration than aluminum powders having strong adhesion at low temperatures, such as as-received powders. Therefore, the higher the onset temperature of strong adhesion, as determined by plotting curves of the type shown in FIGS. 4 and 5, the more desirable the powder for those propellant applications which are greatly influenced by aluminum agglomeration. Alcoa 1230, as-received, shown in FIG. 4, would indicate an undesirable aluminum powder, and treated Alcoa 1230, shown in FIG. 5, would indicate a desirable powder for use as fuel in a propellant grain.

Results of a few test runs using the present invention clearly indicated that the loading or packing of the sample was very important to achieving repeatable results. This is to be expected because packing not only affects the number of contacts between particles, but also the contact area, especially during heating, when the contacts must be considered variable due to thermal expansion. These difficulties are common to experiments with powders which involve mechanical or thermal stress. The steel sphere which has been used in this method had a polished surface, and adhesion between this polished surface and the particles was rather small. Examination of the steel sphere after removal from a sample indicates that a major part of the load was needed to separate aluminum particles from each other rather than to separate particles from the sphere.

Obviously many modifications and variations of the present invention are possible in light of the above teaching. It is therefore to be understood that within the scope of the appended claims the invention may be practiced otherwise than as specifically described. For example, the adhesive properties of any amorphous powder or particulate material, such as ceramic or plastic materials, could be examined using this method and apparatus.

What is claimed is:

1. A method for measuring adhesion of particulate material comprising the steps of:
   filling a container to a first predetermined level with said particulate material;
   packing said particulate material in said container to a first predetermined density;
   resting a geometric object upon said packed particulate material in said container;
   adding more particulate material to said container to a second predetermined level;
   compacting said more particulate material to a second predetermined density;
   pulling the geometric object from said sample of particulate material by measurable force means; and
   measuring the force required to pull said geometric object from said sample of particulate material.

2. A method as set forth in claim 1, further comprising:
   maintaining said sample of particulate material within a predetermined temperature range during said pulling step.

3. A method as set forth in claim 2 wherein said maintaining step comprises:
   heating said sample of particulate material from an initial temperature to a beginning temperature within said predetermined temperature range at a predetermined rate; and
   holding said sample of particulate material within said predetermined temperature range during said pulling and measuring steps.

4. A method as set forth in claim 1 wherein said method is repeated a plurality of times, said sample of particulate material being heated to different predetermined temperatures and maintained within a predetermined temperature range each time during said pulling step, and said measured force being recorded for each predetermined temperature range.

5. Apparatus for measuring adhesion of particulate material comprising:
   a container for holding a sample of particulate material packed to a predetermined density;
   a geometric object configured to be immersed in said sample of particulate material within said container such that said geometric object bonds to said particulate material less than said particulate material bonds to itself;
   measurable force application means attached to said geometric object for pulling said geometric object from said sample of particulate material such that the force measured is the force required to break adhesion bonding between particles of said particulate material; and,
   transducer means attached to said measurable force means for measuring the magnitude of force required to pull said geometric object from said sample of particulate material.

6. Apparatus as set forth in claim 5 further comprising:
   temperature regulation means operating upon said sample of particulate material for controlling the temperature of said sample of particulate material.

7. Apparatus as set forth in claim 6 wherein said temperature regulation means comprises:
   a supply of electric power;
   an electric furnace operative to supply heat to said sample of particulate material;
   a thermocouple positioned to respond to the temperature of said sample of particulate material; and
   a temperature programmer and controller operatively connected to said supply of electric power, said electric furnace, and said thermocouple, and operative to maintain said sample of particulate material at a preselected temperature.

8. Apparatus as set forth in claim 5 wherein said geometric object comprises a spherical body.

9. Apparatus as set forth in claim 8 wherein said spherical body comprises a steel ball.

10. Apparatus as set forth in claim 5 wherein said measurable force application means comprises:
- a wire attached to said geometric object and to said transducer means;
- a syncronous motor configured to wind a line; and
- a line having two ends, attached to said synchronous motor on one end, and attached to said transducer means on the other end.

11. Apparatus as set forth in claim 10 wherein said measurable force means further comprises at least one pulley supported to structure which is rigid relative to said synchronous motor and to aforesaid container, said pulley guiding said line between said synchronous motor and said transducer means;

12. Apparatus as set forth in claim 6 wherein said transducer means comprises a load cell.

13. Apparatus as set forth in claim 5, further comprising:
- a thermcouple positioned to respond to the temperature of said sample of particulate material; and
- recording means attached to said transducer means and to said thermocouple, and operative to record and permanently preserve continuous data corresponding to the measured force magnitude and temperature of said sample of particulate material.

* * * * *